United States Patent [19]

Chorev et al.

[11] Patent Number: 5,149,779
[45] Date of Patent: Sep. 22, 1992

[54] HUMORAL HYPERCALCEMIC FACTOR ANTAGONISTS

[75] Inventors: Michael Chorev, Jerusalem, Israel; Eli Roubini, Lansdale, Pa.

[73] Assignee: Merck & Co., Inc., Rahway, N.J.

[21] Appl. No.: 557,828

[22] Filed: Jul. 26, 1990

[51] Int. Cl.$^5$ .................. C07K 7/54; C07K 7/36; A61K 37/02
[52] U.S. Cl. .................... 530/317; 530/307
[58] Field of Search .............. 530/317, 321, 307; 514/9, 11

[56] References Cited

U.S. PATENT DOCUMENTS

| | | | |
|---|---|---|---|
| 3,886,132 | 5/1975 | Brewer et al. | 260/112.5 |
| 4,086,196 | 4/1978 | Tregear | 260/112.5 |
| 4,423,037 | 12/1983 | Rosenblatt et al. | 424/177 |
| 4,771,124 | 9/1988 | Rosenblatt et al. | 530/324 |

FOREIGN PATENT DOCUMENTS

WOA88/005-96  1/1988  PCT Int'l Appl.

OTHER PUBLICATIONS

Rudinger, Peptide Hormones, Parsons (Ed.), U. Park Press, Baltimore, pp. 1–7 (1976).
Hruby, Life Sciences, vol. 31, pp. 189–199 (1982).
Rosol et al., Chem. Abs., 109, Abs. #32522g, p. 143 (1988).
Kubota et al., J. Endocr., 108, No. 2, pp. 261–265 (1986).
Rosenblatt, N. Engl. J. Med., 315, No. 16, pp. 1004–1013 (1986).
Caporale et al., Characterization of Parathyroid Hormone Antagonists, Peptides, Chemistry and Biology, pp. 449–451 (1987).
Stewart et al., I, Proc. Natl. Acad. Sci. U.S.A., 80, pp. 1454–1458 (Mar. 1983).
Strewler et al., I, J. Clin. Invest., 71, pp. 769–774 (Mar. 1983).
Moseley et al., Proc. Natl. Acad. Sci. U.S.A., 84, pp. 5048–5052 (Jul. 1987).
Strewler et al., II, J. Clin. Invest., 80, pp. 1803–1807 (Dec. 1987).
Stewart et al., II, Biochem. & Biophys. Res. Com., 146, No. 2, pp. 672–678.
Mangin et al., Proc. Natl. Acad. Sci. U.S.A., 85, pp. 597–601 (1988).
Suva et al., Science, 237, pp. 893–896 (1987).
Juppner et al., I, Chem. Abs., 109, Abs. #32806c, p. 143 (1988).
Juppner et al., II, J. Biol. Chem., 263, No. 18, pp. 8557–8560 (1988).
Rodan et al., J. Clin. Invest., 72, pp. 1511–1515 (Oct. 1983).
Kemp et al., Science, 238, pp. 1568–1570 (1987).
Horiuchi et al., Science, 238, pp. 1566–1568 (1987).
Nagasaki et al., Biochem. & Biophys. Res. Com., 158, No. 3, pp. 1036–1042 (1989).
McKee et al., Endocrin., 122, No. 6, pp. 3008–3010 (1988).

Primary Examiner—Y. Christina Chan
Attorney, Agent, or Firm—Carol S. Quagliato; Charles M. Caruso; William H. Nicholson

[57] ABSTRACT

Peptide analogues of human humoral hypercalcemic factor (hHCF) that contain a lactam bridge act as inhibitors of the naturally occurring peptide. A lactam bridge between Lys and Asp situated five residues (inclusive) apart confers rigidity to that region of the peptide, and enhances the helical nature and metabolic stability of the peptide analogue.

3 Claims, No Drawings

HUMORAL HYPERCALCEMIC FACTOR ANTAGONISTS

BACKGROUND OF THE INVENTION

This invention relates to novel humoral hypercalcemic factor (HCF) antagonists having the following general structure:

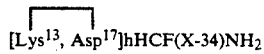

wherein X is 7, 8, 9, 10, or 11, and which encompasses various amino acid substitutions.

Peptide analogues can be used as inhibitors of their naturally occurring peptide counterparts in vivo and in vitro, and may also be useful as inhibitors of other analogous molecules. Peptides bind to their specific cell surface receptors and directly or indirectly cause changes in cell metabolism or physiology. If the cell receptor is blocked, the peptidal effect will also be blocked. A peptide analogue, when administered to a vertebrate such as a mammal, can bind to specific cell surface receptors and thereby block the activity of a corresponding or otherwise related peptide. Peptide analogues are useful in treating various diseases caused by an excess of the naturally occurring peptide and in treating peptide dependent tumors. Peptide analogues that act as antagonists are also useful in vitro in combination with a bioassay for the naturally occurring peptide. One example of this invention relates to the synthesis and use of novel humoral hypercalcemic factor (HCF) analogues that are useful for inhibiting the action of HCF both in vivo and in vitro. Human humoral hypercalcemic factor is designated herein as "hHCF."

Previously, it had been proposed that tumors could secrete parathyroid hormone (PTH) ectopically and cause hypercalcemia of malignancy. However, messenger RNA for PTH was not found in such tumors. Several studies demonstrated that a PTH-like factor, physicochemically and immunologically distinct from PTH and later identified as HCF, is secreted by tumor cells. S. B. Rodan et al., *J. Clin. Invest.*, 72:1511 (1983); A. F. Stewart et al., *Proc. Natl. Acad. Sci. U.S.A.*, 80:1454 (1983); G. J. Strewler et al., *J. Clin. Invest.*, 71:769 (1983). It was also known that this PTH-like factor stimulates adenylate cyclase in PTH target cells, and that this activity can be inhibited by PTH antagonists.

Recently, several investigators isolated and obtained partial amino acid sequences of peptide derived from several different human tumors (lung squamous carcinoma, renal cell carcinoma, and breast carcinoma). J. M. Moseley et al., *Proc. Natl. Acad. Sci. U.S.A.*, 84:5048 (1987); G. J. Strewler et al., *J. Clin. Invest.*, 80:1803 (1987); A. F. Stewart et al., *Biochem. Biophys. Res. Commun.*, 146:672 (1987); M. Mangin et al., *Proc. Natl. Acad. Sci. U.S.A.*, 85:597 (1988). One group published the putative full-length peptide structure (141 amino acids) based on the complementary DNA (cDNA) nucleotide sequence. L. J. Suva et al., *Science*, 237:893 (1987). This new PTH-like factor has been named human "humoral hypercalcemic factor" and is considered to be related in biological effects to PTH. Thus, HCF is currently considered to be a factor responsible for hypercalcemia of malignancy by its secretion from the tumor and its altering effect on calcium metabolism.

HCF shows considerable homology to the biologically critical NH$_2$-terminal region of PTH, a region that is believed to have an alpha helix followed by a beta turn. However, there are significant differences in the peptide sequences between PTH and HCF, and this new factor is the product of a different gene.

Fragments of peptide containing the region specific for binding to the cell surface receptor can be used as inhibitors or blocking agents. For HCF, it is considered that the N-terminal 34 amino acids are sufficient to define binding specificity to the cell surface receptor. The following is the N-terminal 34 amino acid sequence of hHCF: Ala-Val-Ser-Glu-His(5)-Gln-Leu-Leu-His-Asp(10)-Lys-Gly-Lys-Ser-Ile(15)-Gln-Asp-Leu-Arg-Arg-(20)-Arg-Phe-Phe-Leu-His(25)-His-Leu-Ile-Ala-Glu(30)-Ile-His-Thr-Ala. Standard abbreviations well recognized in the peptide chemistry art are utilized herein.

Extensive structure and activity studies have now led to the design of peptide analogues that have high binding affinity for their respective cell surface receptors but do not stimulate the production of second messenger molecules once bound. HCF analogues with two to thirteen amino acids removed from the N-terminus produce inhibitors that still bind with high affinity to the peptide hormone receptor without causing a change in cyclic AMP concentration.

The novel peptide analogues of this invention are HCF antagonists with six to ten amino acids removed from the N-terminus that contain a lactam bridge five residues (inclusive) apart in the alpha helical region of the peptide. The lactam modification confers rigidity to this area of the peptide structure thereby enhancing its helical nature. The lactam bridge also stabilizes the biologically active conformation of the analogues and improves their resistance to metabolic degradation.

It is an object of the present invention to provide novel peptide analogues that act as antagonists of HCF; a peptide analogue of HCF that will bind with the cell surface HCF receptor can be used to block the effect of the naturally occurring peptide. Thus, it is also an object of the present invention to provide peptide analogues useful for the treatment of hypercalcemia of malignancy.

Another object of the present invention is to provide HCF analogues with enhanced alpha-helical nature and rigidity in the NH$_2$-terminal region, and with improved metabolic stability.

Another object of the present invention is to provide HCF analogues wherein amino acid modifications result in binding to the cell surface receptors without activating a second messenger molecule. Still another object of the present invention is to provide methods of inhibiting the action of HCF through the administration of novel HCF analogues. The above and other objects are accomplished by the present invention in the manner more fully described below.

DETAILED DESCRIPTION OF THE INVENTION

The present invention is concerned with novel cyclized peptide analogues of hHCF that have the formula

wherein X is 7, 8, 9, 10 or 11, and a lactam bond bridges two incorporated amino acids that are five residues apart (inclusive) at the 13 and 17 positions. Substitution of D-amino acids for L-amino acids is within the scope of the present invention where such substitutions result in an active peptide.

Additionally, the present invention includes the above novel peptide analogues wherein (a) Ala[34] is substituted by Tyr[34], and/or (b) Phe[23] is substituted by a hydrophobic amino acid selected from the group consisting of the D- or L-stereoisomers of Leu, Nle, Val, Tyr, Trp, beta-naphthylAla and alpha-naphthylAla, and/or (c) Gly[12] is substituted by an amino acid selected from the group consisting of the D- or L-stereoisomers of Trp, Pro, Ala, Aib (aminoisobutyrl), naphthylAla, alpha-MeTrp and N-MeGly, and/or (d) any or each of Asp[10], Lys[11] or Ser[14] is substituted by any N-alkyl containing or D- or L-stereoisomers of any amino acid, in particular Asn, Leu or His, and/or (e) the N-terminal amine is acetylated, or the N-terminal amine is replaced with -H.

A preferred peptide analogue is

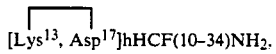
[Lys[13], Asp[17]]hHCF(10-34)NH$_2$.

and the peptide containing the substitutions indicated above where permissible.

Use of the terms "and/or" in the above description of the invention means that the substitutions described can be made singly or in any and all combinations described. For example, each of

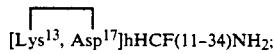
[Lys[13], Asp[17]]hHCF(11-34)NH$_2$;

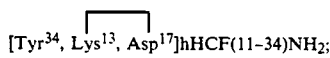
[Tyr[34], Lys[13], Asp[17]]hHCF(11-34)NH$_2$;

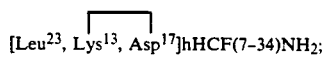
[Leu[23], Lys[13], Asp[17]]hHCF(7-34)NH$_2$;

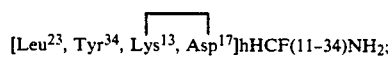
[Leu[23], Tyr[34], Lys[13], Asp[17]]hHCF(11-34)NH$_2$;

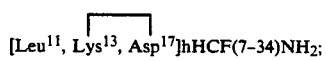
[Leu[11], Lys[13], Asp[17]]hHCF(7-34)NH$_2$;

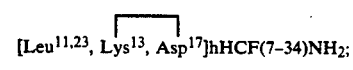
[Leu[11,23], Lys[13], Asp[17]]hHCF(7-34)NH$_2$;

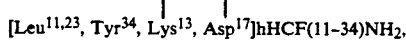
[Leu[11,23], Tyr[34], Lys[13], Asp[17]]hHCF(11-34)NH$_2$.

as well as the other described combinations, are included within the present invention.

The presence of D-amino acids in peptides in place of L-amino acids sometimes results in a peptide resistant to catabolism. However, not all such substitutions result in an active peptide. Thus, such substitutions which result in active peptides are considered to be within the scope of the present invention. The utilization of D-amino acids in peptide hormone synthesis is described in the following publications: Coltrera et al., *Biochemistry*, 19:4380-4385 (1980); Rosenblatt et al., *Biochemistry*, 20:7246-7250 (1981). Additionally, substitutions of amino acids which are equivalent to the amino acids disclosed herein is considered to be within the scope of the present invention.

Any of the above-mentioned peptide analogues can be used in a method of acting upon an HCF receptor which comprises administering any of such peptide analogues in an effective amount to a mammal. Additionally, an in vitro bioassay of HCF wherein a measured amount of such peptide analogue inhibits binding of HCF to an HCF receptor is an aspect of the present invention. A pharmaceutical composition which comprises an effective amount of a novel peptide analogue of this invention and a pharmaceutically acceptable carrier is another feature of this invention.

The present invention also provides a method of inhibiting the action of HCF comprising the administration of a therapeutically effective amount of a novel HCF analogue of this invention. The present invention also provides a method of treating osteoporosis or hypercalcemia comprising the administration of a therapeutically effective amount of a novel HCF analogue described above. A method of treating hyperparathyroidism comprising the administration of a therapeutically effective amount of a novel HCF analogue of this invention is also provided. A method of treating hyperparathyroidism expressed as a hypercalcemic crisis, renal failure, persistent hyperparathyroidism after renal transplantation, or hypertension is also provided. A method of treating the disease state produced by a tumor or other cell overproducing a peptide hormone-like molecule and method of treating immune diseases wherein the disease state comprises inflammation, an allergic response, or hyperactive lymphocytes is also provided by the novel peptide analogues of the present invention.

The balance of the description will be divided into two sections. Section I will describe the preparation and structure of inhibitors of peptide hormones. Section II will discuss the use of the peptide hormone inhibitors.

I. Preparation and Structure of Peptide Hormone Inhibitors

The technique of solid-phase peptide synthesis, developed by Merrifield ("Solid-Phase Peptide Synthesis", *Advances in Enzymology*, 32:221-296 (1969); G. Barany and R. B. Merrifield "Solid-Phase Peptide Synthesis" in *The Peptides*, Vol. 2, editors: E. Gross & J. Meienhofer (1980)) has been successfully employed in the synthesis of peptides including HCF. This method is based on the strategy of having the carboxyl terminus of the peptide linked covalently to a solid support. The desired peptide sequence is prepared by stepwise coupling of single amino acids to a peptide chain growing from the carboxyl toward the amino terminus. Coupling is typically achieved by activation of the carboxyl group of the amino acid being attached to the resin, which may have other potentially reactive groups blocked. Following addition of an amino acid to the growing polypeptide chain, and prior to further chain elongation, the alpha-amino (Boc) protecting group is typically removed. Because each amino acid is coupled by nearly the same series of reactions, the need for elaborate strategies in the synthesis is minimized. Solublility is not a major issue during synthesis, because the peptide is linked to a solid support. This method is rapid and it can be utilized by a single worker. It is very convenient for the synthesis of multiple analogues with amino-terminal substitutions, because a single synthesis can be branched in multiple directions near the amino terminus, thereby creating many analogues varying only in the amino terminal region.

II. Use of Peptide Inhibitors

The method of inhibiting the action of HCF peptide comprises the administration of a therapeutically effective amount of any HCF peptide analogue. These peptide analogues retain specificity for the cell surface receptor without stimulating a physiological response. This method of use applies to the entire peptide or its analogue, or to a fragment of the peptide or analogue containing the receptor binding site.

The use of peptide analogues is exemplified by HCF analogues. The HCF is of human origin but HCF of bovine, rat or any mammalian source may prove to be equivalent to the human HCF. The analogue may contain all the amino acids indicated or additional truncations or elongations. Individual amino acids can be substituted to improve biological or chemical stability.

The peptide analogues of this invention can be used in vitro to measure the concentration of naturally occurring peptide. This bioassay procedure is illustrated by a bioassay for HCF. The unknown concentration of HCF in a solution can be determined by measuring the amount of HCF analogue required to inhibit its binding to the HCF cell surface receptor. The concentration of HCF analogue required to block the action of HCF is a direct indicator of the HCF concentration.

HCF analogues can be used to diagnose the etiology of or to treat osteoporosis or hypercalcemia through the administration of a therapeutically effective amount of the HCF analogues of this invention. Similarly, hyperparathyroidism and other aspects of hyperparathyroidism, such as a hypercalcemic crisis, renal failure, persistent hyperparathyroidism after renal transplantation or hypertension can be treated through the administration of the HCF analogues of this invention.

Tumors and other aberrant cell growth often produce hormone-like substances causing a disease state. The use of peptide analogues to block stimulation caused by such hormone-like substances can result in the alleviation of the disease state. An example of this is the humoral hypercalcemic factor of malignancy. Therefore, the HCF peptide analogues of the present invention can be administered to treat diseases caused by aberrant production of hormone-like substances.

The peptide analogues of this invention exhibit both oral and parenteral activity and can be formulated in dosage forms for oral, parenteral, intra-nasal, or topical administration. Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluent. In the case of capsules, tablets, and pills, the dosage forms may also comprise buffering agents. Tablets and pills can additionally be prepared with an enteric coating.

Liquid dosage forms for oral administration include pharmaceutically acceptable emulsions, solutions, suspensions, syrups and elixers containing inert diluents commonly used in the pharmaceutical art. Besides inert diluents, such compositions can also include adjuvants, such as wetting agents, emulsifying and suspending agents, and sweetening agents. Preparations according to this invention for parenteral administration include sterile aqueous or non-aqueous solutions, suspensions or emulsions. Examples of non-aqueous solvents or vehicles are propylene glycol, polyethylene glycol, vegetable oils such as olive oil and injectable organic esters such as ethyloleate.

The dosage of active ingredient in the compositions of this invention may be varied; however it is necessary that the amount of the active ingredient shall be such that a sutable dosage form is obtained. The selected dosage form is dependent upon a variety of factors, including the desired therapeutic effect, the route of the administration, and the duration of the treatment. Although the dose will vary from patient to patient depending upon the nature and severity of disease, the patient's weight, special diets, concurrent medication and other factors which those skilled in the art will recognize, the dosage range will generally be about 1 to 1000 mg. per patient per day which can be administered in single or multiple doses. Preferably, the dosage range will be about 150 to 250 mg. per patient per day.

Obviously, numerous modifications and variations of the present invention are possible in light of the above teachings. It is therefore to be understood that within the scope of the claims, the invention may be practiced otherwise than as specifically described herein.

EXAMPLE 1

Synthesis and Purification of Peptide Analogues of HCF

Analogues of HCF were prepared by a modification of the solid-phase method of Merrifield. Syntheses were performed using an APPLIED BIOSYSTEMS 430A SYNTHESIZER 4-Methyl-benzhydrylamine hydrochloride resin (polystyrene-1% crosslinked divinylbenzene, USB) was employed as the solid support in order to effect the carboxyamide ($CONH_2$) COOH-terminal modification.

The tertiary butyloxycarbonyl (Boc) group was used to protect the alpha amino group of each amino acid during coupling. Side-function protection was afforded as follows: (a) the hydroxyl group of serine was protected as the O-benzyl ether (Bzl); (b) the hydroxyl group of tyrosine as the 0-2,6-dichlorobenzyl ether (DCB) or p-bromobenzyloxycarbonyl ester (BrZ); (c) the carboxyl group of glutamic acid as the benzyl ester (Bzl); (d) the carboxyl group of aspartic acid as the cyclohexyl (Chx) or the fluorenylmethyl ester (OFm); (e) the imidazole nitrogen of histidine by the benzyloxymethyl (BOM) and the guanidine function of arginine was protected by the p-toluene-sulfonyl (TOS) group, and the indole imine by formyl (For); and (f) the lysine epsilon amino group by 2-chloro-benzyloxycarboxyl (ClZ), or fluorenyl methoxy carbonyl (Fmoc) groups. All amino acids were obtained from Applied Biosystems, Inc., Peninsula Laboratories, or Bachem Chemicals.

The peptide-resin syntheses were carried out using Applied Biosystems, Inc. specified protocols. Double couplings were carried out for the incorporation of each amino acid. After the final coupling of each of the arginines (residues 18-21) the remaining free amino groups were acetylated to prevent generation of deletion peptides. Deprotection times with trifluoroacetic acid (TFA) were extended 6 minutes over manufacturer protocols.

The cyclization of the ε-NH₂ of Lys¹³ to the β-COOH of Asp¹⁷ required the following modifications in the synthetic procedures described previously: 1) incorporation of the Nα-BOC-Asp(β-OFm)-OH in position 17; 2) incorporation of the Nα-BOC-Lys(ε-Fmoc)-OH in position 13; 3) deprotection of the ε-amino Fmoc and β-carboxyl OFm ester and cyclization by coupling of the ε-amino of Lys¹³ to the β-carboxyl of Asp¹⁷.

Coupling of BOC-Asp(β-OFm)-OH (0.82 g, 2.0 mmol) to the free α-amino terminus of side chain protected hHCF(18-34)pMBHA-Ⓡ (0.25 mmol) was carried out in the standard manner (1 mmol of preformed symmetrical anhydride). The recoupling of BOC-Asp(β-OFm)-OH and following coupling up to position 13 were performed in the presence of 5% diisopropylethylamine (DIPEA) in DMF.

Coupling of Boc-Lys(ε-Fmoc)-OH (0.94 g, 2.0 mmol) to the free amino terminus of side chain protected hHCF(14-34)pMBHA-Ⓡ (0.25 mmol) was carried out in the standard manner (1 mmol of preformed symmetrical anhydride). The recoupling of Boc-Lys(ε-Fmoc)-OH was performed in the presence of 5% DIPEA in DMF and followed with consecutive washes: CH₂Cl₂ (1×1 minute) and DMF (1×1 minute).

Removal of ε-Fmoc and β-OFm protecting groups was carried out in the standard manner. The protected resin-bound peptide was treated with 20% piperidine in DMF (1×1 minute followed by 1×20 minutes). The resin was consecutively washed with MeOH (1×1 minute), CH₂Cl₂ (4×1 minute) and DMF (2×1 minute). Cyclization between the ε-amino of Lys¹³ and β-carboxyl of Asp¹⁷ was carried out in the standard manner using the BOP reagent (0.75 mmol) in the presence of 1.5% DIPEA in DMF. Two consecutive couplings were carried out and followed by a sequence of washes: CH₂Cl₂ (1×1 minute), DMF (1×1 minute), MeOH (1×1 minute), CH₂Cl₂ (1×1 minute) and MeOH (1×1 minute). Testing with ninhydrin indicated the completion of the reaction, which was then followed by further washings: CH₂Cl₂ (4×1 minute) and DMF (2×1 minute).

The peptide was cleaved from the copolymer resin with simultaneous removal of the side-chain protecting groups similar to the 2 step HF cleavage procedure described by Tam, J.A.C.S., 105: 6442-6455 (1983). In the first HF step the following ratios of reagents were used: 5% p-cresol, 5% p-thiocresol, 65% dimethyl sulfide and 25% HF. 10 ml of mixture per gram of peptide-resin was used for 2 hours at 0° C. In the second HF step the following ratio of reagents were used: 5% p-cresol, 5% p-thiocresol and 90% HF. The cleavage was carried out for 75 min. at 0° C. After removal of HF the peptide-resin mixture was washed with anhydrous ether to remove scavenger. The peptide was then extracted with 50% acetic acid and water. The washes were combined and chromatographed using SEPHADEX G-50F, eluting with 50% HOAc.

After combining fractions containing product, removal of solvent in vacuo and lyophilization, the partially purified peptide was chromatographed by reverse phase HPLC (VYDAC C₄ bonded silica, 15μ particle size, 300A pore size, using aqueous acetonitrile gradient containing 0.1% TFA).

EXAMPLE 2

BRCM Binding Assay Results

HCF analogues were analysed in a new receptor assay (Goldman et al., Endocrinol., 123: 1468-1475 (1988)) which modified the assay reported in Rosenblatt et al., Endocrinol., 107: 545-550 (1980). The binding assay used [Nle⁸,¹⁸(¹²⁵I)-Tyr³⁴] bPTH(1-34)NH₂ which was purified by HPLC (NOVAPAK C₁₈, 32-35% CH₃CN in 0.1% TFA) and was stored as aliquots in 25 mM TrisHCl/1% BSA at −70° C. Bovine renal cortical plasma membranes (BRCM) were incubated with radioligand (25,000 cpm) in the absence or presence of HCF analogues in a Tris-containing buffer (250 ul) for 30 min. at 21° C. Once equilibrium was reached, bound and free radioligand were separated by centrifugation. High specific binding (85%) to bovine renal cortical membranes was obtained consistently.

| Structure | Binding $K_b$ (nM) |
|---|---|
| [Lys¹³, Asp¹⁷]hHCF(7-34)NH₂ | 14.8 ± 1.6 |
| [Lys¹³, D—Asp¹⁷]hHCF(7-34)NH₂ | 1060 ± 170 |
| [D—Lys¹³, Asp¹⁷]hHCF(7-34)NH₂ | 420 ± 57 |
| [D—Lys¹³, D—Asp¹⁷]hHCF(7-34)NH₂ | 1990 ± 500 |

EXAMPLE 3

BRCM Adenylate Cyclase Assay Results

HCF analogues were analyzed in a bovine renal cortical membrane (BRCM) adenylate cyclase assay as described in Horiuchi et al., Science, 238: 1566 (1987); Goldman et al., Endocrinol., 123(5): 1468-1475 (1988). 3 nM [Nle⁸,¹⁸,Tyr³⁴]bPTH(1-34)NH₂ was used to stimulate adenylate cyclase.

| Structure | Adenylate Cyclase $K_J$ (nM) |
|---|---|
| [Lys¹³, Asp¹⁷]hHCF(7-34)NH₂ | 127.6 ± 17.2 |
| [Lys¹³, D—Asp¹⁷]hHCF(7-34)NH₂ | >10 μm |
| [D—Lys¹³, Asp¹⁷]hHCF(7-34)NH₂ | 1332 ± 237 |
| [D—Lys¹³, D—Asp¹⁷]hHCF(7-34)NH₂ | >10 μm |
| [Leu¹¹, D—Trp¹², Lys¹³, Asp¹⁷] hHCF(7-34)NH₂ | 47 ± 3 |

EXAMPLE 4

Human Bone (B-10) Cell Binding Assay Results

HCF analogues were analyzed were analyzed in a human osteosarcoma cell line, B10, for the ability to inhibit the binding of [Nle⁸,¹⁸(¹²⁵I)-Tyr³⁴]bPTH- (1-34)NH$_2$ by the method described by R. L. McKee et al., *Endocrinol.*, 122: 3008 (1988).

| Structure | Binding K$_b$ (nM) |
|---|---|
| [Lys$^{13}$, Asp$^{17}$]hHCF(7-34)NH$_2$ | 19 ± 2 |
| [Lys$^{13}$, D—Asp$^{17}$]hHCF(7-34)NH$_2$ | 1390 ± 130 |
| [D—Lys$^{13}$, Asp$^{17}$]hHCF(7-34)NH$_2$ | 357 ± 24 |
| [D—Lys$^{13}$, D—Asp$^{17}$]hHCF(7-34)NH$_2$ | 1372 ± 340 |

EXAMPLE 5

Human Bone Cell (B10) Adenylate Cyclase Assay Results

HCF analogues were analyzed in a human osteosarcoma cell line, B10, for the ability to inhibit cAMP stimulation by 1 nM [Nle$^{8,18}$,Tyr$^{34}$]bPTH(1-34)NH$_2$ by the method described by R. J. Majeska et al., *Endocrinol.*, 107: 1494 (1980).

| Structure | Adenylate Cyclase K$_I$ (nM) |
|---|---|
| [Lys$^{13}$, Asp$^{17}$]hHCF(7-34)NH$_2$ | 17.4 ± 5.5 |
| [Lys$^{13}$, D—Asp$^{17}$]hHCF(7-34)NH$_2$ | 900 ± 60 |
| [D—Lys$^{13}$, Asp$^{17}$]hHCF(7-34)NH$_2$ | 354 ± 35 |
| [D—Lys$^{13}$, D—Asp$^{17}$]hHCF(7-34)NH$_2$ | 378 ± 100 |
| [Leu$^{11}$, D—Trp$^{12}$, Lys$^{13}$, Asp$^{17}$]hHCF(7-34)NH$_2$ | 3.2 ± 1.0 |
| CH$_3$CO[Leu$^{11}$, D—Trp$^{12}$, Lys$^{13}$, Asp$^{17}$]hHCF(10-34)NH$_2$ | 3.6 ± 0.8 |

What is claimed is:

1. A peptide having the following structure:

[Lys$^{13}$, Asp$^{17}$]hHCF(X-34)NH$_2$ wherein X is 7, 8, 9, 10, or 11 and wherein (a) Ala$^{34}$ is replaced by Tyr$^{34}$, and/or (b) Phe$^{23}$ is replaced by a hydrophobic amino acid selected from the group consisting of the D- or L-stereoisomers of Leu, Nle, Val, Tyr, Trp, beta-naphthylAla and alpha-naphthylAla, and/or (c) Gly$^{12}$ is replaced by an amino acid selected from the group consisting of the D- or L-stereoisomers of Trp, Pro, Ala, Aib, naphthylAla, alpha-MeTrp and N-MeGly and/or (d) any or each of Asp$^{10}$, Lys$^{11}$ or Ser$^{14}$ is replaced by an amino acid selected from the group consisting of the D- or L-steroisomers of Asn, Leu and His, and/or (e) the N-terminal amine is acetylated.

2. The peptide of claim 1 which is

[Leu$^{11}$, D—Trp$^{12}$, Lys$^{13}$, Asp$^{17}$]hHCF(7-34)NH$_2$.

3. The peptide of claim 1 which is

CH$_3$CO[Leu$^{11}$, D—Trp$^{12}$, Lys$^{13}$, Asp$^{17}$]hHCF(10-34)NH$_2$.

* * * * *